(12) United States Patent
Maeda et al.

(10) Patent No.: US 8,266,973 B2
(45) Date of Patent: Sep. 18, 2012

(54) AUTOMATIC SAMPLER AND METHOD FOR INJECTING SAMPLE

(75) Inventors: Yoshiaki Maeda, Kyoto (JP); Takaaki Fujita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 968 days.

(21) Appl. No.: 12/254,717

(22) Filed: Oct. 20, 2008

(65) Prior Publication Data

US 2009/0100942 A1    Apr. 23, 2009

(30) Foreign Application Priority Data

Oct. 23, 2007    (JP) .................... 2007-274669

(51) Int. Cl.
*G01N 1/14* (2006.01)
(52) U.S. Cl. .................... 73/864.11; 73/864.21
(58) Field of Classification Search ............... 73/864.11, 73/864.21, 864.86
See application file for complete search history.

(56) References Cited

U.S. PATENT DOCUMENTS

| | | | |
|---|---|---|---|
| 3,529,475 A * | 9/1970 | Muhlestein et al. ....... | 73/864.16 |
| 4,721,137 A | 1/1988 | Müller | |
| 5,194,226 A * | 3/1993 | Tomoff et al. ................ | 422/509 |
| 5,400,666 A * | 3/1995 | Song .......................... | 73/864.21 |

FOREIGN PATENT DOCUMENTS

| | | |
|---|---|---|
| CN | 2938104 Y | 8/2007 |
| JP | 2003-215118 A | 7/2003 |

OTHER PUBLICATIONS

The First Office Action for the Application No. 200810170890.5 from State Intellectual Property Office of People's Republic of China dated May 6, 2011.
The Second Office Action for the Application No. 200810170890.5 from The State Inteliectual Property Office of People's Republic of China dated Nov. 3, 2011.

* cited by examiner

*Primary Examiner* — Hezron E Williams
*Assistant Examiner* — Nashmiya Fayyaz
(74) *Attorney, Agent, or Firm* — Cheng Law Group, PLLC

(57) ABSTRACT

After a sampling needle is moved to a position above a sample container, the sampling needle is moved down so that the tip of the sampling needle penetrates a septum, and is then preferably moved down to a position at which the tip of the sampling needle is not brought into contact with a sample contained in the sample container, and then, the sampling needle is once elevated until the sampling needle is pulled out of the septum, and is then again moved down to penetrate the septum until the tip of the sampling needle is inserted into the sample to suck the sample through a suction port of the sampling needle, and then, the sampling needle is moved to a sample injection port of an analyzer to inject the sample into the analyzer.

12 Claims, 7 Drawing Sheets

AUTOMATIC SAMPLER AND METHOD FOR INJECTING SAMPLE

BACKGROUND OF THE INVENTION

1. Field of the Invention

The present invention relates to an automatic sampler for injecting a sample through a sampling needle into an analysis flow path of an analyzer such as a liquid chromatograph, and a method for injecting a sample with the use of such an automatic sampler.

2. Description of the Related Art

In an automatic sampler for a liquid chromatograph, a sampling needle is moved down toward a sample container so as to penetrate a septum hermetically sealing the sample container. Then, a predetermined amount of a sample is sampled from the sample container by sucking the sample through the tip of the sampling needle, and the sample is injected into an analysis flow path of the liquid chromatograph (see Japanese Patent Application Laid-open No. 2003-215118).

A sample container is usually sealed with a highly airtight septum to prevent the volatilization of a sample and the entry of foreign matter. Such a septum is made of a material through which a sampling needle can penetrate. At the time of sample suction, a sampling needle is allowed to penetrate a septum so that the tip of the sampling needle is inserted into a sample container, and then a sample is sucked through the sampling needle.

A conventional method for sucking a sample through a sampling needle will be described with reference to FIG. 7. The top of a sample container 3 placed in a rack is covered with a septum 26 made of an aluminum seal and the like to prevent the vaporization of a sample 24 contained in the sample container 3 and the entry of foreign matter from outside. A sampling needle 5 is moved to a position above the sample container 3 to suck the sample 24 (see (a)). Then, the sampling needle 5 is moved down so as to penetrate the septum 26 (see (b)), and is then further inserted into the sample container 3 to suck the sample 24 (see (c) and 7(d)).

As shown in FIG. 7(b), the septum 26 is largely bent in a direction in which the sampling needle 5 is inserted into the sample container 3 (i.e., in a downward direction) in the course of penetration of the sampling needle 5 through the septum 26, and is then returned to its initial state at the moment of complete penetration of the sampling needle 5 through the septum 26. Due to such deformation of the septum 26, there is a case where air pressure in the sample container 3 is changed so that air enters a sample suction port of the sampling needle 5. If air enters the sample suction port of the sampling needle 5, the amount of the sample to be sucked is reduced by the amount of air. In this case, there is a problem that the amount of the sample to be sucked is smaller than a predetermined amount so that a peak area value obtained as a measurement value becomes smaller.

As one measure to solve such a problem, a sampling needle having a groove formed on the outer circumferential surface thereof has been used. In this case, even when the sampling needle penetrates a septum, air can enter and exit a sample container through the groove located between the sampling needle and the septum. However, it is difficult to polish such a grooved sampling needle, and therefore the surface roughness of the groove portion of the sampling needle is greater than that of the outer circumferential surface of the sampling needle. For this reason, the groove portion is poor in liquid repellency, and therefore if a sample is adhered to the groove portion, the sample is likely to remain there. Therefore, the grooved sampling needle is inferior to a sampling needle having a simple cylindrical shape in carry-over performance. Further, in the use of the grooved sampling needle, there is a problem that contamination is caused by a sample remaining in the groove portion.

SUMMARY OF THE INVENTION

It is therefore an object of the present invention to provide an automatic sampler which can allow a sampling needle to penetrate a septum hermetically sealing a sample container to suck a sample while preventing the occurrence of a problem, such as contamination, as well as a problem caused by a change in air pressure in the sample container that occurs when the sampling needle penetrates the septum.

The automatic sampler according to the present invention includes a sampling needle for penetrating a septum of a sample container and entering the sample container to suck a sample contained in the sample container through its tip, a drive unit for driving the sampling needle, and a control unit for controlling the operation of the drive unit. As shown in FIG. 2, the control unit includes a septum penetration means 30, a sample suction means 32 and a sample injection means 34, and operates the septum penetration means 30, the sample suction means 32 and the sample injection means 34 in this order.

The septum penetration means 30 moves the sampling needle down until the tip of the sampling needle penetrates a septum, and then elevates the sampling needle to a position, at which the tip of the sampling needle is pulled out of the septum, without carrying out the suction of a sample through the sampling needle. Such an operation carried out by the septum penetration means 30 may be continuously repeated more than once.

The sample suction means 32 moves the sampling needle down to allow the tip of the sampling needle to penetrate the septum, and further moves the sampling needle down until the tip of the sampling needle is inserted into a sample contained in the sample container to suck the sample.

The sample injection means 34 pulls the sampling needle out of the septum and then moves the sampling needle to an injection port of an analyzer to inject the sample into an analysis flow path of the analyzer.

The septum penetration means 30 preferably moves the sampling needle down so that the tip of the sampling needle is only moved down to a level at which the tip is not brought into contact with a sample contained in the sample container. If the sample is adhered to a sample suction port of the sampling needle before sample suction, the amount of the sample to be sucked becomes larger by the amount of the sample adhered to the sample suction port, which affects a measurement value obtained by analysis. By preventing a sample from being adhered to the sample suction port of the sampling needle before sample suction, it is possible to suck a precise amount of the sample at the time of sample suction.

The sample suction means 32 preferably moves the sampling needle down at a position displaced in a horizontal plane from a position at which the sampling needle is moved down by the septum penetration means 30. In this case, the sampling needle moved down by the sample suction means 32 penetrates a septum at a position displaced from the position of a through hole formed in the septum by the downward movement of the sampling needle by the septum penetration means 30, and therefore air can enter and exit a sample container through the through hole formed in the septum by the downward movement of the sampling needle by the septum penetration means 30 so that pressure in the sample container is more reliably prevented from being changed before sample suction.

Since the automatic sampler according to the present invention can prevent a change in pressure in a sample container, the automatic sampler can use a sampling needle having a cylindrical external form and not having been subjected to processing for forming, on its outer circumferential surface, a groove or the like through which air can enter and exit a sample container. Such a sampling needle having a cylindrical external form can be easily polished, and is therefore superior to a grooved sampling needle in preventing carry-over and contamination.

Further, the control unit may have a first operation mode in which the septum penetration means 30, the sample suction means 32 and the sample injection means 34 are operated in this order, and a second operation mode in which the sample suction means 32 and the sample injection means 34 are operated in this order without the septum penetration means 30 being operated. In this case, either the first or the second operation mode is selected.

As a septum for hermetically sealing a sample container, a disposable one or a reusable one is used. A disposable septum is made of aluminum, polyethylene, polypropylene, or the like. When the sampling needle penetrates such a disposable septum once, a through hole is formed in the disposable septum and remains even after the sampling needle is pulled out of the septum. A reusable septum is made of an elastic material such as silicone rubber. Therefore, a through hole formed by the sampling needle in such a reusable septum is closed due to the elasticity of the septum after the sampling needle is pulled out of the septum. This makes it possible to reuse the septum. In a case where a disposable septum is used to hermetically seal a sample container, the influence of a change in pressure in the sample container can be eliminated by operating the septum penetration means 30. In a case where a reusable septum is used, however, an effect obtained by operating the septum penetration means 30 cannot be obtained because even when the septum penetration means 30 is operated, a through hole formed in the septum is closed by pulling the sampling needle out of the septum and therefore pressure in the sample container is again changed when the sample suction means 32 allows the tip of the sampling needle to penetrate the septum. Therefore, in a case where a reusable septum is used, the second operation mode, in which the sample suction means 32 and the sample injection means 34 are operated in this order without the septum penetration means 30 being operated, is efficient. For this reason, a preferred embodiment of the automatic sampler according to the present invention has the first operation mode and the second operation mode, either of which can be selected.

A method for injecting a sample according to the present invention includes the following steps S1 to S3 to be carried out in this order using an automatic sampler having a sampling needle to penetrate a septum of a sample container and to enter the sample container to suck a sample contained in the sample container through its tip and to inject the sample into an analyzer:

(step S1) a septum penetration step in which the sampling needle is moved down until the tip of the sampling needle penetrates the septum, and is then elevated to a position, at which the tip of the sampling needle is pulled out of the septum, without carrying out the suction of the sample through the sample needle;

(step S2) a sample suction step in which the sampling needle is moved down to allow the tip of the sampling needle to penetrate the septum, and is further moved down until the tip of the sampling needle is inserted into the sample contained in the sample container to suck the sample; and (step S3) a sample injection step in which the tip of the sampling needle is pulled out of the septum, and the sampling needle is moved to an injection port of the analyzer to inject the sample into an analysis flow path of the analyzer.

The septum penetration step S1 may be continuously repeated.

In the downward movement of the sampling needle in the step S1, it is preferred that the tip of the sampling needle is only moved down to a level at which the tip is not brought into contact with the sample contained in the sample container.

In the downward movement of the sampling needle in the step S2, the position of the sampling needle may be displaced in a horizontal plane from the position of the sampling needle moved down in the step S1.

The sample injection method may have a first operation mode in which the steps S1 to S3 are carried out in this order and a second operation mode in which the steps S2 and S3 are carried out in this order without the step S1 being carried out. In this case, either the first or the second operation modes may be selected to operate.

In the sample injection method and the automatic sampler according to the present invention, the sampling needle is moved down so as to penetrate a septum hermetically sealing a sample container so that a through hole is formed in the septum, and then the sampling needle is once pulled out of the septum without sucking a sample, and then the sampling needle is again moved down so as to penetrate the septum to suck a sample contained in the sample container. By using a septum in which a through hole formed by allowing the sampling needle to penetrate the septum once can be kept open, it is possible to eliminate a drawback of sucking a sample through the sampling needle in which air is contained in its suction port, resulting from a change in pressure in a sample container that occurs when the sampling needle penetrates the septum to suck a sample. This makes it possible to improve quantitativeness in sucking a sample through the sampling needle.

DETAILED DESCRIPTION OF THE INVENTION

Figure 1:
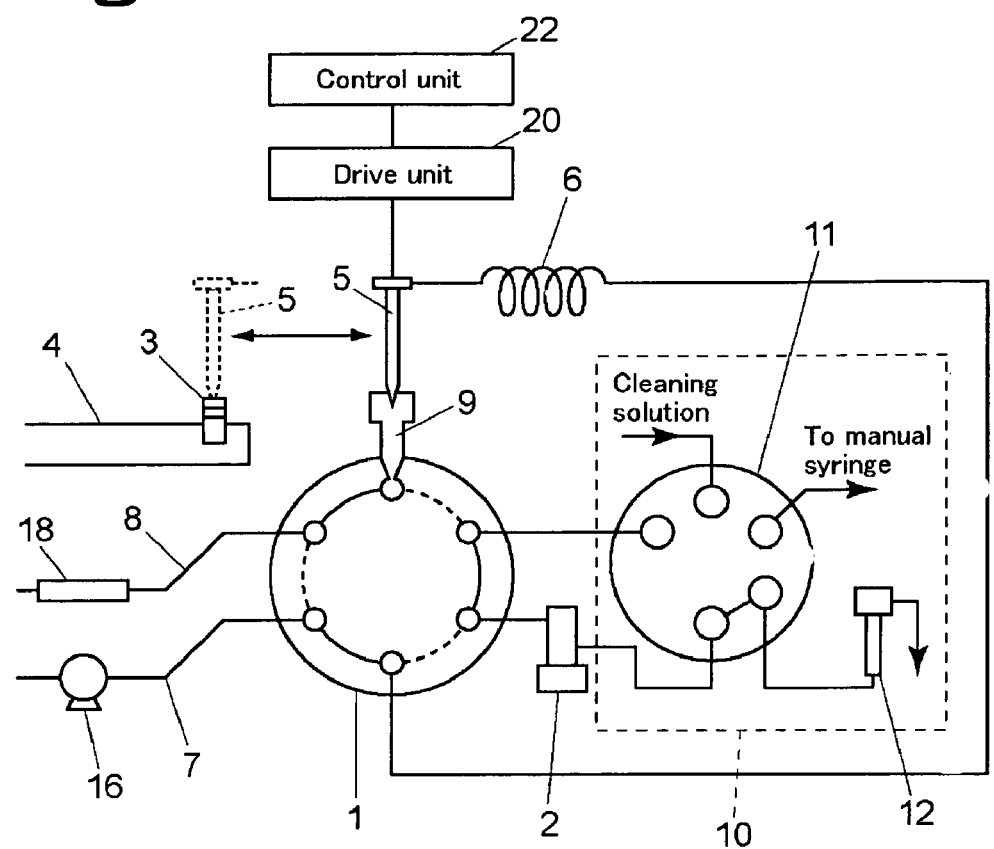
FIG. 1 is a schematic view showing the flow path configuration of one embodiment of an automatic sampler for a liquid chromatograph.

FIG. 1 is a schematic view showing the flow path configuration of one embodiment of an automatic sampler for a liquid chromatograph.

A rotary 6-port 2-position flow path switching valve 1 has 6 ports arranged at regular intervals. The position of each path for allowing two adjacent ports to communicate with each other is moved by rotating a rotor to switch flow paths to be connected to the adjacent two ports.

A sample (liquid) as an object to be analyzed is contained in a sample container 3 placed on a rack 4. A sampling needle 5 is connected to a pump 2 through a looped flexible conduit (hereinafter, referred to as a "loop") 6 and the flow path switching valve 1. The pump 2 gives suction force to the sampling needle 5. The sampling needle 5 is moved by a drive unit 20. The control unit 22 controls the drive unit 20 to control the movement of the needle 5, and controls a pump 16 to control the suction and discharge of a sample through the needle 5.

The needle 5 sucks a sample at a position indicated by a broken line in FIG. 1 (sampling position), and then the needle 5 is moved to a position indicated by a solid line (injection position) and inserted into an injection port 9. After the needle 5 is inserted into the injection port 9, liquid tightness between the needle 5 and the injection port 9 is maintained. The injection port 9 is directly attached and connected to the flow path switching valve 1.

A mobile phase of a liquid chromatograph is discharged from the liquid delivery pump 16, and then passes through a mobile phase delivery flow path 7 and the flow path switching valve 1, and further flows into a column 18 through a flow path 8 located upstream of the column 18. A cleaning system 10 includes another valve (low-pressure valve) 11 and a cleaning port 12. The cleaning system 10 cleans a system for sampling including the needle 5 prior to the analysis of a next sample to prevent contamination caused by the previous sample.

Figure 2:
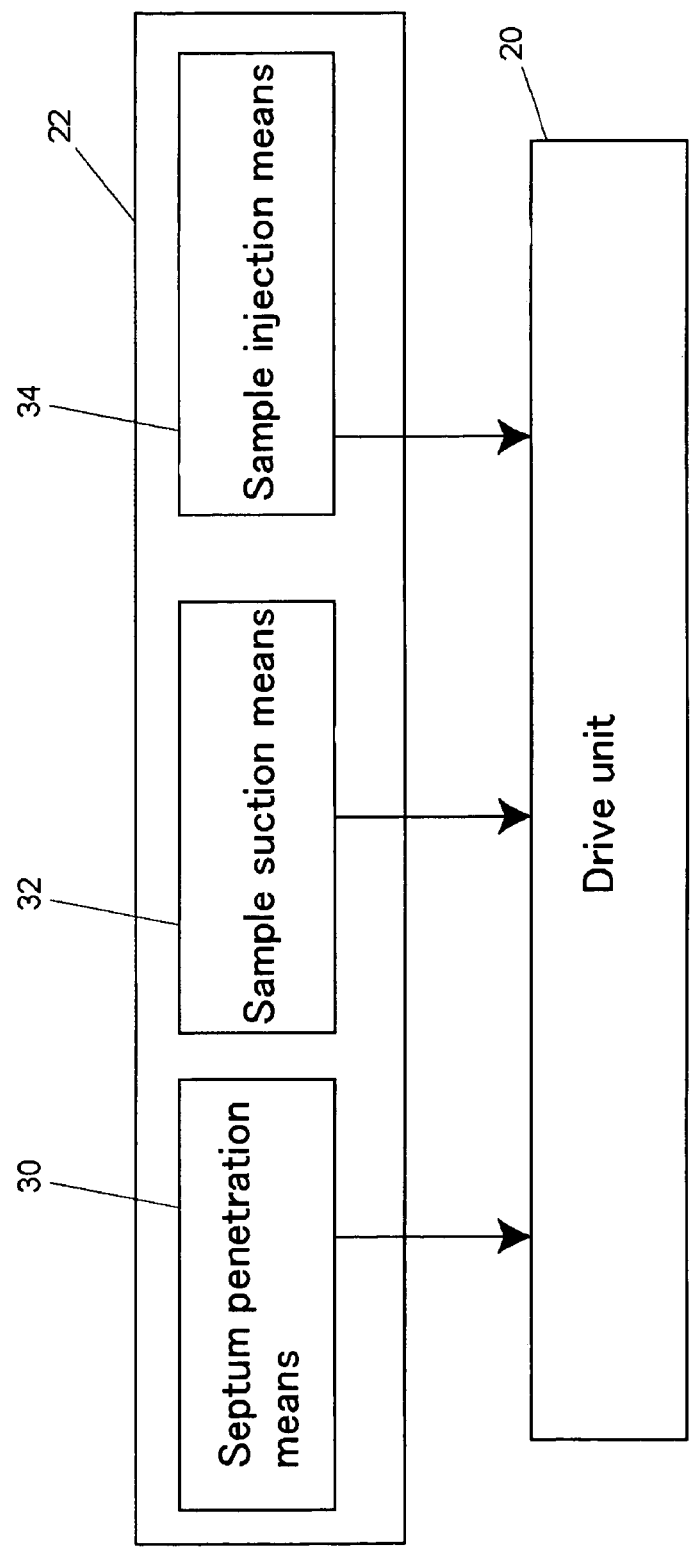
FIG. 2 is a block diagram schematically showing a control unit of the automatic sampler according to the present invention.

As shown in FIG. 2, the control unit 22 includes a septum penetration means 30, a sample suction means 32, and a sample injection means 34. The control unit 22 may have, as an operation mode for operating these means, only a first operation mode in which the septum penetration means 30, sample suction means 32 and the sample injection means 34 are operated in this order. The control unit 22 may also have, in addition to the first operation mode, a second operation mode in which the sample suction means 32 and the sample injection means 34 are operated in this order without the septum penetration means 30 being operated. In this case, the control unit 22 can also select either the first or the second operation modes.

The control unit 22 can be realized by a computer dedicated to the automatic sampler, a computer dedicated to an analyzer, such as a liquid chromatograph, using the automatic sampler, or a personal computer for general purpose use.

Figure 6:
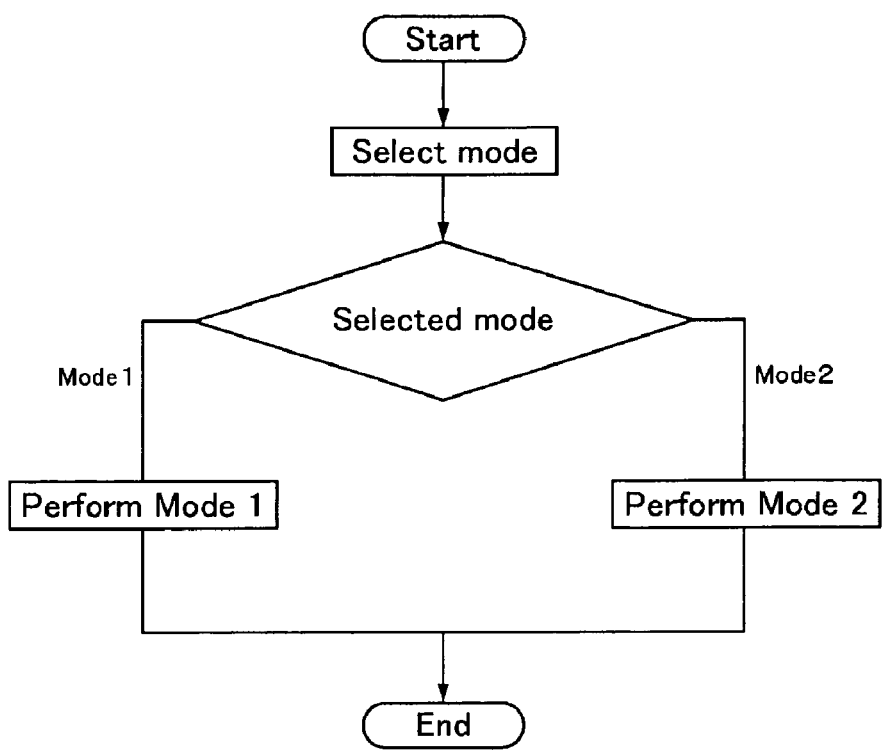
FIG. 6 is a flow chart showing the overall flow of the process of sucking a sample using the automatic sampler according to the embodiment shown in FIG. 1.
Figure 7:
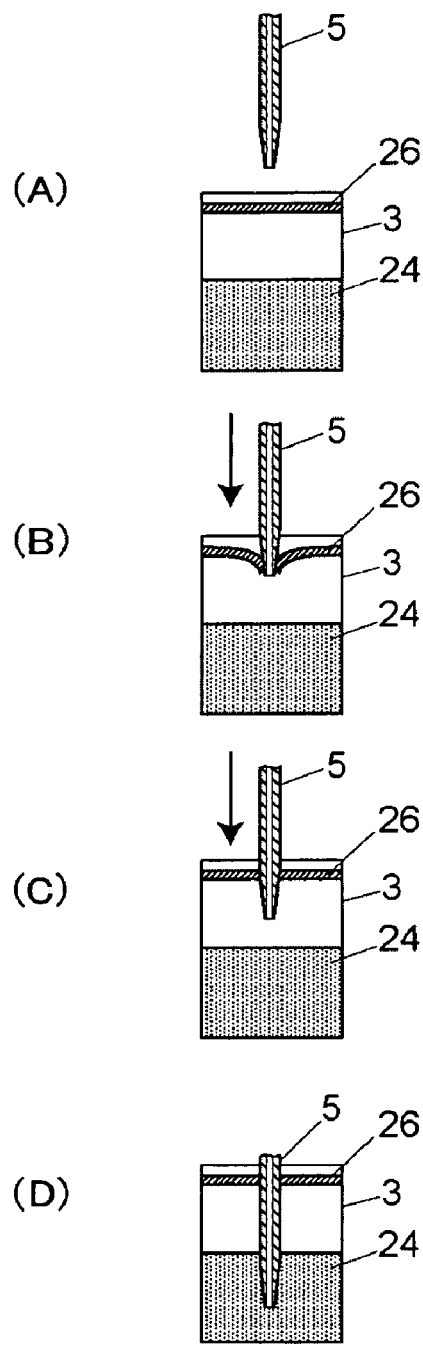
FIG. 7(A) to FIG. 7(D) are sectional views illustrating the steps of the process of sucking a sample using a conventional automatic sampler.

Hereinbelow, the operation of the automatic sampler according to this embodiment will be described. As shown in FIG. 6, the automatic sampler has two operation modes for sucking a sample and injecting the sample into an analyzer, and carries out one operation mode selected from the two operation modes. More specifically, when an analyst selects one operation mode of the automatic sampler at the start of analysis, the automatic sampler automatically injects a sample into an injection port of an analyzer according to the selected operation mode. In a case where the sample container 3 is hermetically sealed with a disposable septum such as an aluminum seal, operation mode 1 is preferably selected. In a case where a reusable septum made of an elastic material such as silicone is used, operation mode 2 is preferably selected.

Figure 3:
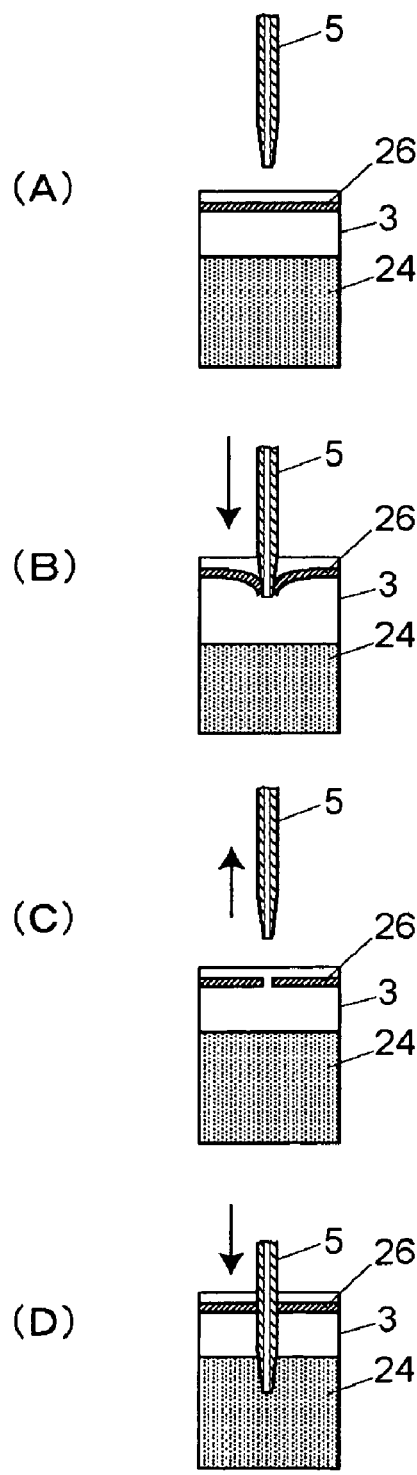
FIG. 3(A) to FIG. 3(D) are sectional views illustrating the steps of one example of the process of sucking a sample using the automatic sampler according to the embodiment shown in FIG. 1.
Figure 4:
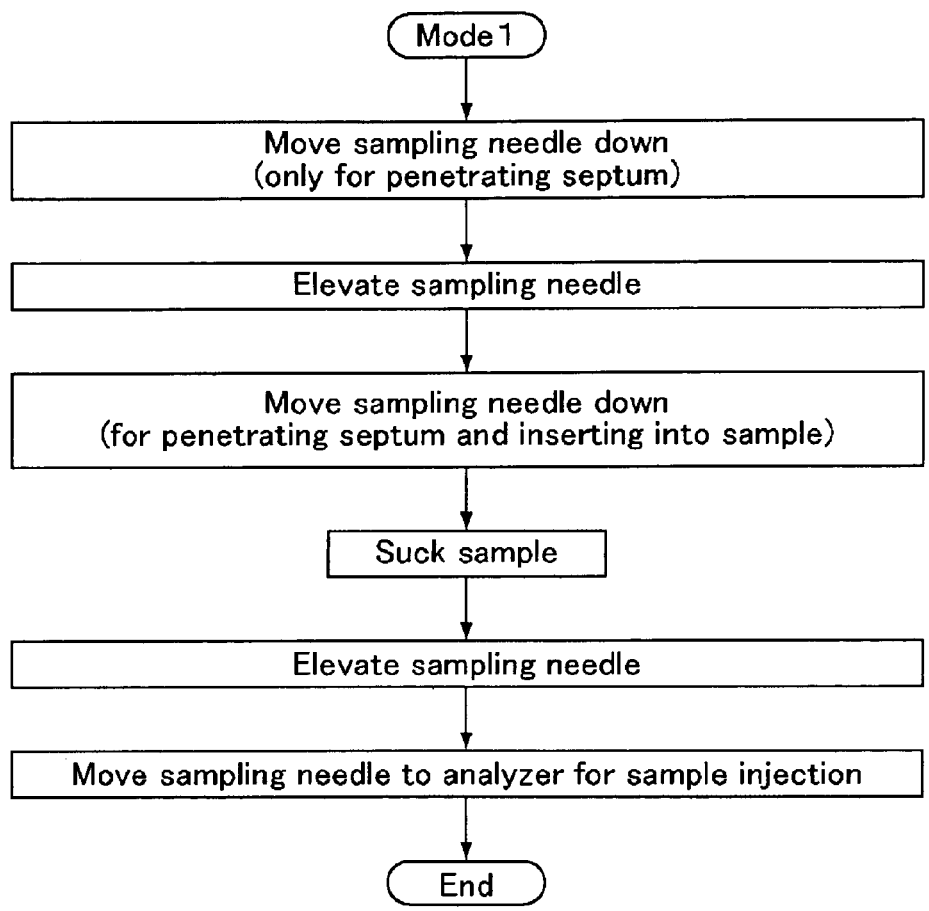
FIG. 4 is a flow chart showing one operation mode for sucking a sample using the automatic sampler according to the embodiment shown in FIG. 1.

First, the operation mode 1 will be described with reference to FIG. 3 showing sectional views illustrating the steps of the operation mode 1 and FIG. 4 showing the flow chart of the operation mode 1.

The top of the sample container 3 is covered with a septum 26 made of such as an aluminum seal to prevent the evaporation of a sample 24 contained in the sample container 3 and the entry of foreign matter from outside.

The movement of the needle 5 is driven by the drive unit 20 controlled by the control unit 22. The operation of sucking and discharging a sample through the needle 5 is controlled by the pump 2 controlled by the control unit 22.

(A) The needle 5 is moved to a position above the sample container 3.

(B) The needle 5 is moved down until the tip of the needle 5 penetrates the septum 26. When the needle 5 penetrates the septum 26, the septum 26 is largely bent in a direction where the needle 5 is inserted into the sample container 3, and is then returned to its initial state, and therefore a sudden change in air pressure occurs in the sample container 3. Here, it is to be noted that the downward movement of the needle 5 is preferably controlled so that the tip of the needle 5 is only moved down to a level at which the tip is not brought into contact with the sample 24. According to the above, it is possible to prevent the sample from being adhered to the needle 5 in the downward movement not intended to suck the sample.

(C) The needle 5 is elevated until the needle 5 is pulled out of the septum 26. According to this operation, air pressure in the sample container 3 is returned to normal. Further, air which has been inserted into a suction port of the needle 5 by allowing the needle 5 to penetrate the septum 26 is discharged from the needle 5.

(D) The needle 5 is again moved down so as to penetrate the septum 26, and then the tip of the needle 5 is inserted into the sample 24 to suck the sample 24. In the downward movement, the position of the needle 5 may be displaced in a horizontal plane from the position of the needle 5 in the previous downward movement. According to the above, it is possible to use a through hole formed in the septum 26 by the previous downward movement as an air hole, thereby more reliably preventing a change in air pressure in the sample container 3.

The sample sucked through the tip of the needle 5 is temporarily stored in the loop 6, and then the needle 5 is elevated until the needle 5 is pulled out of the septum 26. Then, the needle 5 is moved to the injection port 9 to inject the sample stored in the loop 6 into the injection port 9.

Figure 5:
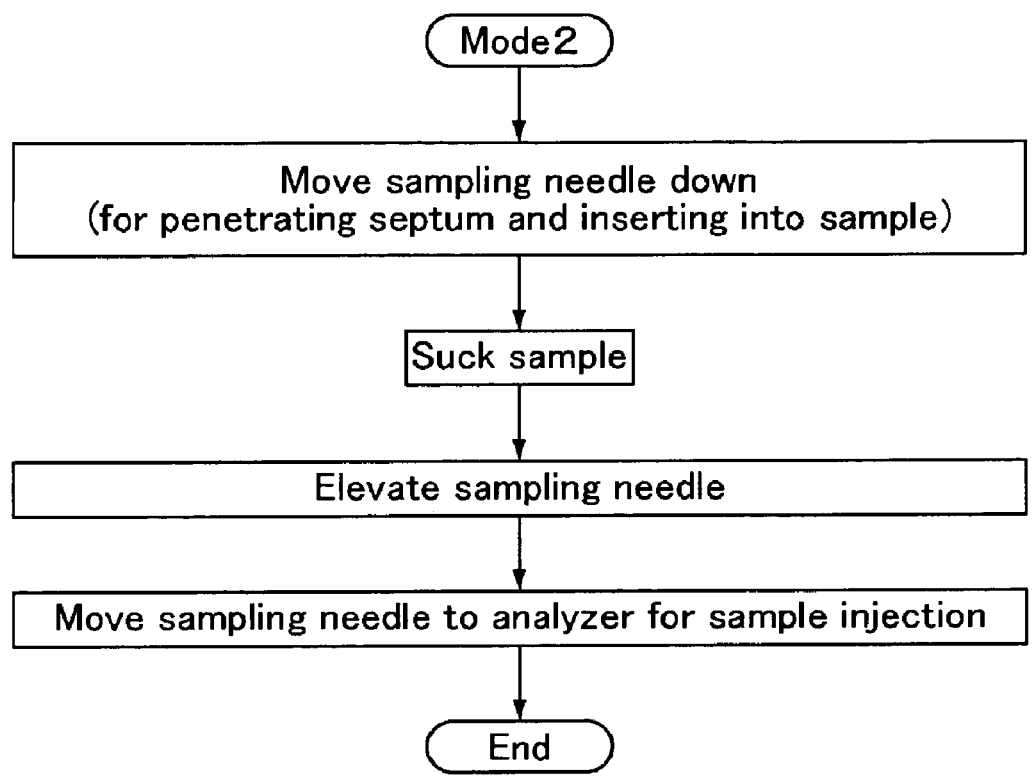
FIG. 5 is a flow chart showing the other operation mode for sucking a sample using the automatic sampler according to the embodiment shown in FIG. 1.

Hereinbelow, the operation mode 2 will be described. In the operation mode 2, a sample is sucked by a one-time downward movement of the needle 5, and is then injected into an injection port of an analyzer. More specifically, as shown in FIG. 5, the needle 5 located above the sample container 3 is moved down so as to penetrate a septum, and is further moved down until the tip of the needle 5 is inserted into a sample to suck the sample. The sample sucked through the needle 5 is stored in the loop 6, and then the needle 5 is elevated until the needle 5 is pulled out of the septum. Then, the needle 5 is moved to an injection port of an analyzer to inject the sample stored in the loop 6 into the injection port 9.

The automatic sampler has the operation mode 1 and the operation mode 2, either of which is selectively carried out. However, the automatic sampler having the operation mode 1 and the operation mode 2 may be configured so that only the operation mode 1 is carried out. Alternatively, the automatic sampler may be configured to have only the operation mode 1.

As described above, since the needle 5 penetrating the septum 26 hermetically sealing the sample container 3 is once pulled out of the sample container 3 to eliminate the influence of a change in air pressure in the sample container 3 that occurs when the needle 5 penetrates the septum 26 and then the needle 5 is again inserted into the sample container 3 to suck the sample 24, it is possible to prevent a mistake in sample suction caused by a change in air pressure in the sample container 3. In addition, it is also possible to improve quantitativeness in sample suction. Therefore, it is possible to obtain stable peak area values in continuous analysis using a liquid chromatograph, and it is also possible to reduce carryover.

Here, it is to be noted that the automatic sampler according to the present invention can be used not only for a liquid chromatograph but also for an analyzer for analyzing a sample injected into a predetermined position from a sample container.

What is claimed is:

1. An automatic sampler comprising:
   a sampling needle for penetrating a septum of a sample container and entering the sample container to suck a sample contained in the sample container through its tip;
   a drive unit for driving the sampling needle; and
   a control unit for controlling the operation of the drive unit, the control unit comprising
   septum penetration means for carrying out at least one cycle including moving the sampling needle down until the tip of the sampling needle penetrates the septum followed by elevating the sampling needle to a position, at which the tip of the sampling needle is pulled out of the septum, without carrying out the suction of the sample through the sampling needle,
   sample suction means for moving the sampling needle down to allow the tip of the sampling needle to penetrate the septum until the tip of the sampling needle is inserted into the sample contained in the sample container to suck the sample, the sample suction means controlling the sampling needle such that the sampling needle only sucks the sample when inserted into the sample, and
   sample injection means for pulling the sampling needle out of the septum and then moving the sampling needle to an injection port of an analyzer to inject the sample into an analysis flow path of the analyzer, and
   the control unit operating the septum penetration means, the sample suction means and the sample injection means in this order,
   wherein each of the septum penetration means, the sample suction means, and the sample injection means are computer readable instructions processed by the control unit, and
   wherein the sampling needle is discharged of air prior to the sucking of the sample.

2. The automatic sampler according to claim 1, wherein the septum penetration means moves the sampling needle down so that the tip of the sampling needle is only moved down to a level at which the tip is not brought into contact with the sample contained in the sample container.

3. The automatic sampler according to claim 1, wherein the sample suction means moves the sampling needle down at a position displaced in a horizontal plane from the position of the sampling needle moved down by the septum penetration means.

4. The automatic sampler according to claim 1,
   wherein the septum penetration means moves the sampling needle down so that the tip of the sampling needle is only moved down to a level at which the tip is not brought into contact with the sample contained in the sample container, and
   wherein the sample suction means moves the sampling needle down at a position displaced in a horizontal plane from the position of the sampling needle moved down by the septum penetration means.

5. The automatic sampler according to claim 1, wherein the sampling needle has a cylindrical external form.

6. The automatic sampler according to claim 1,
   wherein the control unit comprises a first operation mode, in which the septum penetration means, the sample suction means and the sample injection means are operated in this order, and a second operation mode, in which the sample suction means and the sample injection means are operated in this order without the septum penetration means being operated, and
   wherein the control unit can select either mode.

7. A method for injecting a sample using an automatic sampler, the automatic sampler comprising a sampling needle for entering a sample container by penetrating a septum of the sample container to suck a sample contained in the sample container through its tip and then injecting the sample into an analyzer, the method comprising the following steps S1 to S3 to be carried out in this order;
   (step S1) septum penetration step for carrying out moving the sampling needle down until the tip of the sampling needle penetrates the septum followed by elevating the sampling needle to a position, at which the tip of the sampling needle is pulled out of the septum, without carrying out the suction of the sample through the sampling needle;
   (step S2) sample suction step for moving the sampling needle down to allow the tip of the sampling needle to penetrate the septum until the tip of the sampling needle is inserted into the sample contained in the sample container to suck the sample, the sampling needle only sucking the sample when inserted into the sample during the sample suction step; and
   (step S3) sample injection step for pulling the sampling needle out of the septum and then moving the sampling needle to an injection port of an analyzer to inject the sample into an analysis flow path of the analyzer,
   wherein the sampling needle is discharged of air prior to the sucking of the sample.

8. The method for injecting a sample according to claim 7, wherein the septum penetration step S1 is continuously repeated more than once.

9. The method for injecting a sample according to claim 7, wherein in the downward movement of the sampling needle in the step S1, the tip of the sampling needle is only moved down to a level at which the tip is not brought into contact with the sample contained in the sample container.

10. The method for injecting a sample according to claim 7, wherein in the step S2, the position of the sampling needle to be moved down is displaced in a horizontal plane from the position of the sampling needle moved down in the step S1.

11. The method for injecting a sample according to claim 7,
    wherein in the downward movement of the sampling needle in the step S1, the tip of the sampling needle is only moved down to a level at which the tip is not brought into contact with the sample contained in the sample container, and
    wherein in the step S2, the position of the sampling needle to be moved down is displaced in a horizontal plane from the position of the sampling needle moved down in the step S1.

12. The method for injecting a sample according to claim 7,
    wherein the method comprises a first operation mode, in which the steps S1 to S3 are carried out in this order, and a second operation mode, in which the steps S2 and S3 are carried out in this order without the step S1 being carried out, and
    wherein the method can select either mode.

* * * * *